United States Patent
Song et al.

(10) Patent No.: US 9,267,882 B2
(45) Date of Patent: Feb. 23, 2016

(54) APPARATUS FOR DETECTING ORGANIC COMPOUNDS AND APPARATUS FOR MANUFACTURING DISPLAY DEVICE USING THE SAME

(71) Applicant: Samsung Display Co., Ltd., Yongin, Gyeonggi-Do (KR)

(72) Inventors: Eun-Ju Song, Yongin (KR); Hun-Jung Yi, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 142 days.

(21) Appl. No.: 14/226,543

(22) Filed: Mar. 26, 2014

(65) Prior Publication Data

US 2014/0290089 A1 Oct. 2, 2014

(30) Foreign Application Priority Data

Mar. 27, 2013 (KR) ........................ 10-2013-0033061

(51) Int. Cl.
*F26B 3/20* (2006.01)
*G01N 21/3504* (2014.01)

(52) U.S. Cl.
CPC .................................. *G01N 21/3504* (2013.01)

(58) Field of Classification Search
CPC ............... F26B 3/00; F26B 3/20; F26B 5/00; F26B 9/00; B05C 5/02; B05C 19/02; B05C 9/08; B08B 3/00; B08B 7/00
USPC ......... 34/275, 465, 171; 118/610, 719; 134/1, 134/1.1, 1.3
See application file for complete search history.

(56) References Cited

U.S. PATENT DOCUMENTS

| | | | | |
|---|---|---|---|---|
| 3,231,985 A * | 2/1966 | Smith, Jr. | ................ | F26B 3/283 34/448 |
| 6,125,549 A * | 10/2000 | Pikus | ...................... | F26B 3/205 34/135 |
| 6,553,689 B2 * | 4/2003 | Jain | ....................... | F26B 25/006 162/204 |
| 6,649,268 B1 * | 11/2003 | Komine | .............. | C03B 19/1415 359/642 |
| 7,032,324 B2 * | 4/2006 | Kolb | ........................ | B05C 9/10 34/430 |
| 8,898,930 B2 * | 12/2014 | Godot | ...................... | F26B 5/04 134/1 |
| 2003/0106239 A1 * | 6/2003 | Yi | ..................... | H01L 21/67034 34/444 |
| 2004/0010932 A1 * | 1/2004 | Chon | ................ | H01L 21/02052 34/267 |
| 2006/0005422 A1 * | 1/2006 | Yi | ..................... | H01L 21/67253 34/526 |
| 2014/0290089 A1 * | 10/2014 | Song | .................. | G01N 21/3504 34/267 |

FOREIGN PATENT DOCUMENTS

| | | | |
|---|---|---|---|
| EP | 0-182-564 A2 | | 5/1986 |
| JP | 07-174695 A | | 7/1995 |
| JP | 2003-507703 A | | 2/2003 |
| JP | 2006024931 A | * | 1/2006 |

* cited by examiner

*Primary Examiner* — Stephen M Gravini
(74) *Attorney, Agent, or Firm* — Lee & Morse, P.C.

(57) ABSTRACT

An apparatus for detecting an organic compound and an apparatus for manufacturing a display device, the apparatus for detecting an organic compound including an infrared light emitting unit that irradiates infrared rays toward a gas-phase organic compound used as a process gas in an atmospheric pressure equipment; a first window that separates the organic compound from the infrared light emitting unit; an infrared detection unit that measures an infrared absorbance of the organic compound; and a second window that separates the organic compound from the infrared detection unit, wherein infrared absorption regions of the first window and the second window are different from an infrared absorption region of the organic compound.

17 Claims, 10 Drawing Sheets

APPARATUS FOR DETECTING ORGANIC COMPOUNDS AND APPARATUS FOR MANUFACTURING DISPLAY DEVICE USING THE SAME

RELATED APPLICATIONS

Korean Patent Application No. 10-2012-0033061, filed in the Korean Intellectual Property Office on Mar. 27, 2012, is incorporated by reference herein in its entirety.

BACKGROUND

1. Field

Embodiments relate to an apparatus for detecting an organic compound and an apparatus for manufacturing a display device using the same.

2. Description of the Related Art

As a flat panel display, a liquid crystal display (LCD) and an organic light emitting diode (OLED) display have been widely used. The liquid crystal display and the organic light emitting diode display may include a thin film transistor and a capacitor that configure a pixel circuit, a scan driving unit and a data driving unit that control driving of a pixel, a gate wire and a data wire that connect the pixel circuit to the driving units, and the like.

As a process of manufacturing a display device, there are processes performed within atmospheric pressure equipment and using a gas-phase organic compound as a process gas. For example, in a cleaning or drying process that is performed after a wet process, e.g., dry etching, alcohol-based materials, e.g., isopropyl alcohol, may be used as a solvent.

The above information disclosed in this Background section is only for enhancement of understanding of the background of the described technology and therefore it may contain information that does not form the prior art that is already known in this country to a person of ordinary skill in the art.

SUMMARY

An exemplary embodiment provides an apparatus for detecting an organic compound, including: an infrared light emitting unit that irradiates infrared rays toward a gas-phase organic compound used as a process gas in an atmospheric pressure equipment; a first window that separates the organic compound from the infrared light emitting unit; an infrared detection unit that measures an infrared absorbance of the organic compound; and a second window that separates the organic compound from the infrared detection unit. Infrared absorption regions of the first window and the second window may be different from an infrared absorption region of the organic compound.

The organic compound may include an alcohol-based material and the first window and the second window may include a silica-based material. The first window and the second window may include any one of glass and quartz. The first window and the second window may have an infrared transmittance of 0.7 or more in a wavenumber range of 2,800 $cm^{-1}$ to 3,000 $cm^{-1}$.

The second window may include: a pair of support plates including any one of glass and quartz; and a filter disposed between the pair of support plates. The filter may be made of glass including calcium carbonate. An infrared absorption region of the filter may correspond to an infrared absorption region of moisture.

The infrared light emitting unit and the infrared detection unit may be disposed to face each other, having a first part of the atmospheric pressure equipment therebetween. The first window and the second window may be disposed at both sides of the first part via a close and seal member.

The infrared light emitting unit and the infrared detection unit may be disposed in parallel at one side of the first part of the atmospheric pressure equipment and a reflector may be disposed at the other side of the first part. The first window and the second window may be disposed in parallel at one side of the first part via the close and seal member and an inner surface of the reflector facing the first window and the second window may be concavely formed.

Another exemplary embodiment provides an equipment or apparatus for manufacturing a display device, including: a main device for cleaning or drying a substrate; a supply pipe that supplies a gas-phase alcohol-based organic compound to the main device; a discharge pipe that discharges an organic compound used for cleaning; an apparatus for detecting an organic compound that is disposed in the discharge pipe; and an equipment control circuit that is electrically connected to the apparatus for detecting an organic compound. The apparatus for detecting an organic compound may include a first window and a second window including any one of quartz and glass, an infrared light emitting unit that irradiates infrared rays to an organic compound in the discharge pipe through the first window, and an infrared detection unit that measures an infrared absorbance of the organic compound through the second window.

The second window may further include a filter made of glass including calcium carbonate. The supply pipe may be provided with a flow control valve and the equipment control circuit may be electrically connected to the flow control valve and control an operation of the flow control valve depending on information on a concentration of the organic compound provided from the apparatus for detecting an organic compound.

Yet another exemplary embodiment provides an equipment or apparatus for manufacturing a display device, including: a process chamber that has a gas-phase alcohol-based organic compound included in an inner space thereof and cures a polymer material; an apparatus for detecting an organic compound that is disposed in the process chamber; and an equipment control circuit that is electrically connected to the apparatus for detecting an organic compound. The apparatus for detecting an organic compound may include a first window and a second window including any one of quartz and glass, an infrared light emitting unit that irradiates infrared rays to an organic compound in the process chamber through the first window, and an infrared detection unit that measures an infrared absorbance of the organic compound through the second window.

The second window may further include a filter made of glass including calcium carbonate. The equipment control circuit may be electrically connected to an equipment interlock device and control an operation of the equipment interlock device depending on information on a concentration of the organic compound provided from the apparatus for detecting an organic compound.

DETAILED DESCRIPTION

Hereinafter, the embodiments will be described more fully hereinafter with reference to the accompanying drawings, in which exemplary embodiments are shown. As those skilled in the art would realize, the described embodiments may be modified in various different ways, all without departing from the spirit or scope of the embodiments.

In the specification, unless explicitly described to the contrary, the word "comprise" and variations such as "comprises" or "comprising", will be understood to imply the inclusion of stated elements but not the exclusion of any other elements. Further, in the specification, it will be understood that when an element such as a layer, film, region, or substrate is referred to as being "on" another element, it can be directly on the other element or intervening elements may also be present. Further, in the specification, the word "on" means positioning on or below the object portion, but does not essentially mean positioning on the upper side of the object portion based on a gravity direction.

Figure 1:
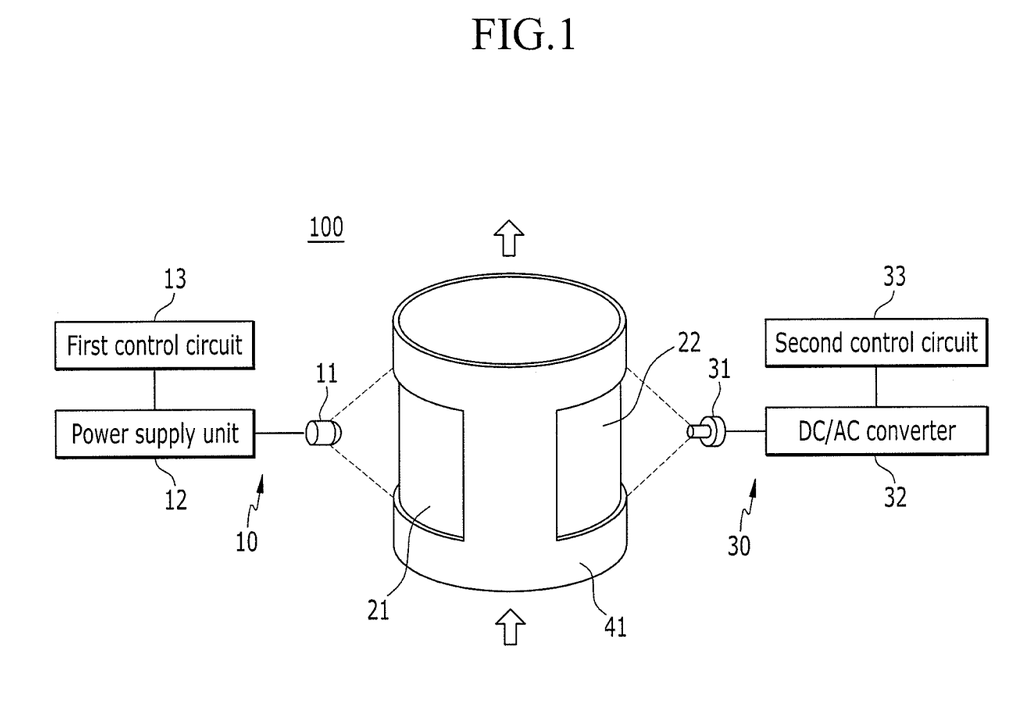
FIG. 1 illustrates a schematic diagram of an apparatus for detecting an organic compound according to a first exemplary embodiment.
Figure 2:
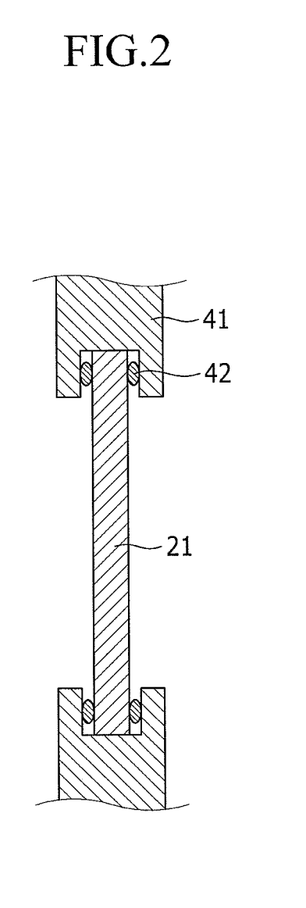
FIG. 2 illustrates a cross-sectional view of a first window of the apparatus of FIG. 1.
Figure 3:
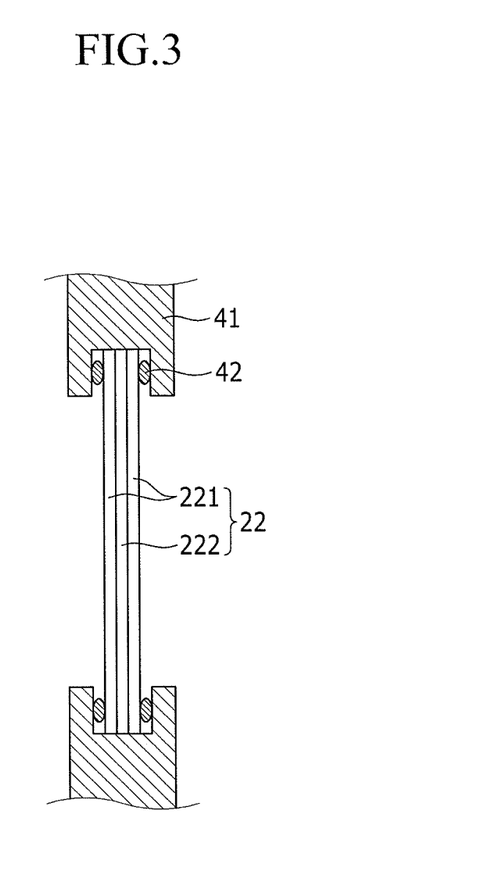
FIG. 3 illustrates a cross-sectional view of a second window of the apparatus of FIG. 1.

FIG. 1 illustrates a schematic diagram of an apparatus for detecting an organic compound according to a first exemplary embodiment, and FIGS. 2 and 3 illustrate cross-sectional views of a first window and a second window of FIG. 1.

Referring to FIGS. 1 to 3, an apparatus 100 for detecting an organic compound according to a first exemplary embodiment may include an infrared light emitting unit 10, a first window 21, an infrared detection unit 30, and a second window 22. The apparatus 100 for detecting an organic compound may detect a concentration of an organic compound in real time by irradiating infrared rays toward an organic compound located within an atmospheric pressure equipment and measuring an infrared absorbance of the organic compound.

The atmospheric pressure equipment in which the apparatus 100 for detecting an organic compound is mounted may be an apparatus using a gas-phase organic compound as a process gas, e.g., a cleaning apparatus, a drying apparatus, an oven, a furnace or other manufacturing equipment or apparatus using alcohol-based materials, e.g., isopropyl alcohol, as a process gas.

The apparatus 100 for detecting an organic compound may be mounted in a first part of the atmospheric pressure equipment. The first part may be an exhaust pipe connected to a cleaner or a drier or a process chamber, e.g., an oven or a furnace. FIG. 1 illustrates, e.g., a case in which the apparatus 100 for detecting an organic compound is mounted in an exhaust pipe 41 through which an organic compound is discharged.

The infrared light emitting unit 10 may irradiate infrared rays toward the organic compound in the exhaust pipe 41, and the infrared detection unit 30 may measure the infrared absorbance of the organic compound to which the infrared rays are irradiated. In an implementation, the infrared light emitting unit 10 and the infrared detection unit 30 may be disposed to face each other, having the exhaust pipe 41 therebetween. The first window 21 may be disposed at one side of the infrared light emitting unit 10 toward the organic compound, and the second window 22 may be disposed at one side of the infrared detection unit 30 toward the organic compound.

The first window 21 and the second window 22 may be directly disposed in the exhaust pipe 41. For example, two openings for mounting the first window 21 and the second window 22, respectively, may be formed in the exhaust pipe 41. The first window 21 and the second window 22 may be disposed in the opening of the exhaust pipe 41 via a close and seal member 42, e.g., an O-ring. The close and seal member 42 may prevent the organic compound in the exhaust pipe 41 from being leaked to the outside of the exhaust pipe 41.

The infrared light emitting unit 10 may include an infrared light emitting element 11, a power supply unit 12, and a first control circuit 13. The power supply unit 12 may provide power that is required to operate the infrared light emitting element 11, and the first control circuit 13 may control the operation of the power supply unit 12.

The infrared detection unit 30 may include an infrared detector 31, an AC/DC converter 32, and a second control circuit 33. The infrared detector 31 may be configured of a quantum detector or a thermal detector. The quantum detector may use a photovoltaic effect or a photoconductive effect to detect infrared rays, and the thermal detector may use a thermoelectromotive effect, a superconductive effect, or a thermal conductive effect to detect infrared rays.

The first window 21 and the second window 22 may serve as a window that isolates the infrared light emitting unit 10 and the infrared detection unit 30 from the organic compound and transmits infrared rays. Therefore, the first window 21 and the second window 22 may not affect the measurement of infrared absorbance of the organic compound, while having high chemical resistance against the organic compound.

The first window 21 and the second window 22 may be made of a material having an infrared absorption region, e.g., different from the infrared absorption region of the organic compound. For example, the apparatus 100 for detecting an organic compound may detect alcohol-based organic compounds, and the first window 21 and the second window 22 may be made of silica-based materials, e.g., glass or quartz, having an infrared absorption region different from an absorption region of alcohol-based organic compounds.

Figure 4:
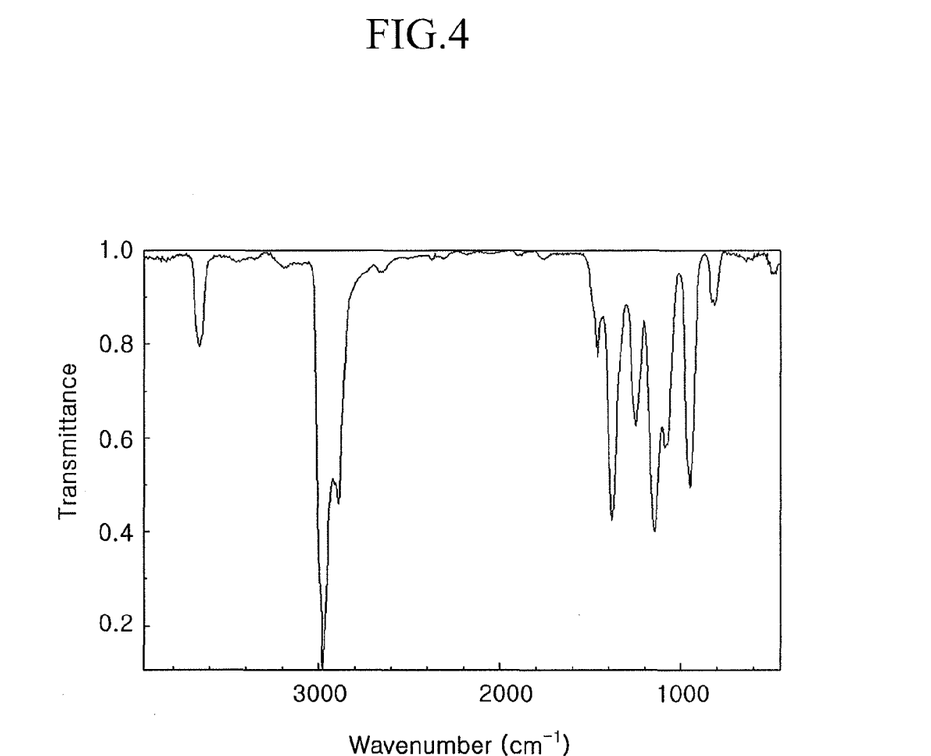
FIG. 4 illustrates a graph of an infrared absorption characteristic of isopropyl alcohol.

FIG. 4 illustrates a graph of an infrared absorption characteristic of isopropyl alcohol. In the graph of FIG. 4, a horizontal axis represents a wavenumber having a reverse relationship to a wavelength, and a vertical axis represents an infrared transmittance and is in inverse proportion to the infrared absorbance.

Referring to FIG. 4, in the case of isopropyl alcohol, a maximum infrared absorbance is represented in a range of approximately 2,800 $cm^{-1}$ to 3,000 $cm^{-1}$. In the atmospheric pressure equipment to which the apparatus for detecting an organic compound according to the exemplary embodiment is applied, the alcohol-based organic compound used as the process gas may have an infrared absorbance similar to that shown in FIG. 4.

Figure 5:
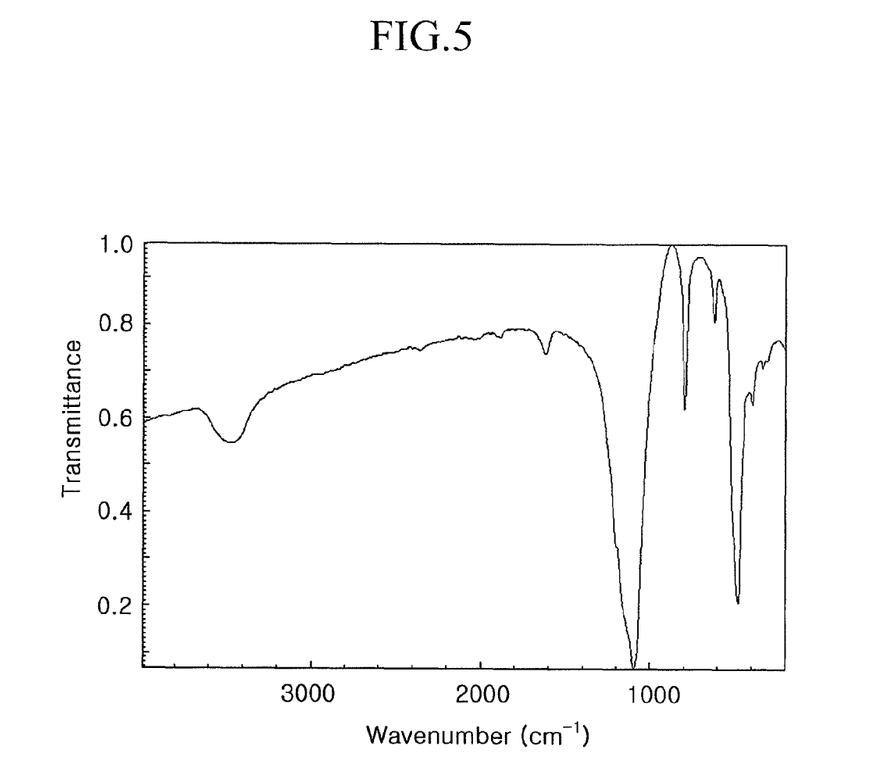
FIG. 5 illustrates a graph of an infrared absorption characteristic of glass.

FIG. 5 illustrates a graph of an infrared absorption characteristic of glass used as the first window and the second window.

Referring to FIG. 5, in the case of glass, the maximum infrared absorbance is represented in a region of approximately 1,000 $cm^{-1}$ to 1,200 $cm^{-1}$. It may be appreciated from the graphs of FIGS. 4 and 5 that the infrared absorption region of glass and the infrared absorption region of the alcohol-based organic compounds are different from each other.

Further, in the case of glass, a transmittance of 0.5 or more is represented in a wavenumber higher than 1,200 $cm^{-1}$, e.g., a high transmittance of about 0.7 is represented in a region of 2,800 $cm^{-1}$ to 3,000 $cm^{-1}$. As such, the first window and the second window made of glass represent the high transmittance in the infrared absorption region of the organic compound, and thus may not affect the detection of the organic compound.

Referring back to FIGS. 1 to 3, the infrared light emitting unit 10 may irradiate infrared rays to the organic compound in the exhaust pipe 41 through the first window 21. The infrared detection unit 30 may measure the infrared absorption wavelength of the organic compound through the second window 22, to detect the concentration of the organic compound in real time.

When molecules absorb infrared rays, vibration and rotation occur, and the infrared absorption wavelengths are each different due to the vibration and rotation of molecules every specific functional group. An infrared spectroscopy is a spectroscopy that observes at which wavelength the absorption of light occurs to know the functional group of the compound, thereby analyzing a structure (kind) of the polymer and the organic compound. Further, the strength (absorbance) of infrared absorption has a relationship with the concentration of constituents, thereby analyzing the concentration of the organic compound depending on the infrared absorbance.

Therefore, the apparatus 100 for detecting an organic compound may rapidly provide the information regarding whether the process gas is being supplied or whether the concentration of the process gas is reduced during the operation of the atmospheric pressure equipments to an operator, thereby helping to prevent the process defect. Further, the apparatus 100 for detecting an organic compound may be connected to an equipment control circuit of the atmospheric pressure equipment to stop the atmospheric pressure equipment or to control the supply amount of the organic compound.

In the apparatus 100 for detecting an organic compound as described above, the first window 21 and the second window 22 made of the silica-based materials may have high chemical resistance against the alcohol-based organic compounds Therefore, the durability and use lifespan of the apparatus 100 for detecting an organic compound may increase.

Further, the second window 22 may include at least one filter that increases the sensitivity of the infrared detection unit 30. For example, the second window 22 may include a pair of support plates 221 (made of silica-based materials) and at least one filter 222 between the pair of support plates 221. FIG. 3 illustrates a case in which one filter 222 is disposed between the pair of support plates 221.

The filter 222 may have an infrared absorption region corresponding to, e.g., overlapping, an infrared absorption region of the material to be intercepted, and represents a high transmittance for the infrared absorption region (approximately 2,800 $cm^{-1}$ to 3,000 $cm^{-1}$) of the alcohol-based organic compounds. Therefore, the filter 222 may intercept the specific wavelength to thereby increase the sensitivity of the infrared detection unit 30 without affecting the detection of the alcohol-based organic compounds.

In the atmospheric pressure equipment using the alcohol-based organic compound as the process gas, moisture ($H_2O$) may be the observed material in addition to the organic compound. The filter 222 may include calcium carbonate and may intercept a wavelength corresponding to an infrared absorption region of moisture, e.g., water. The filter 222 may be made of glass including calcium carbonate.

Figure 6:
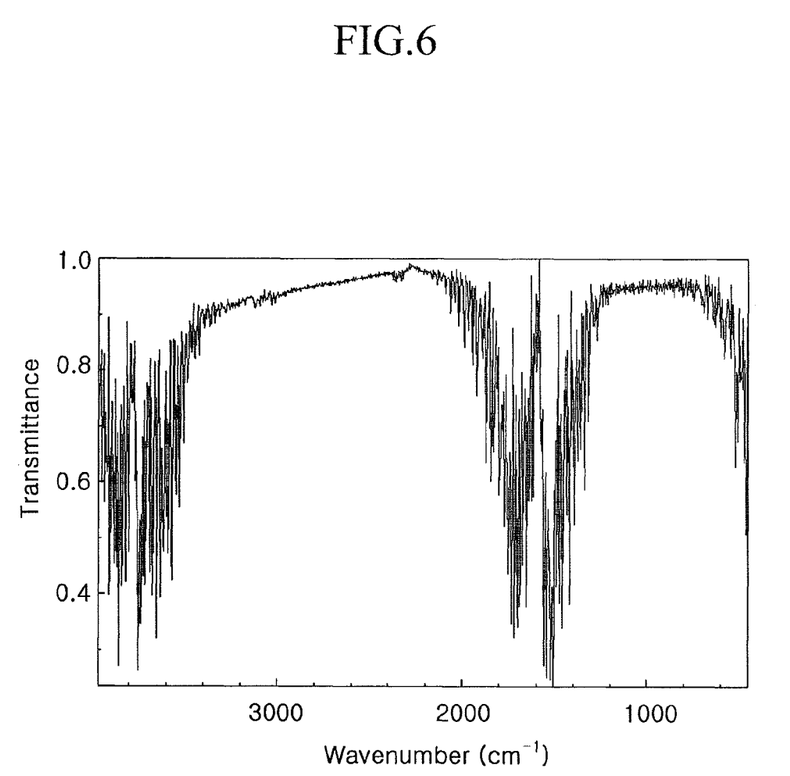
FIG. 6 illustrates a graph of an infrared absorption characteristic of moisture.
Figure 7:
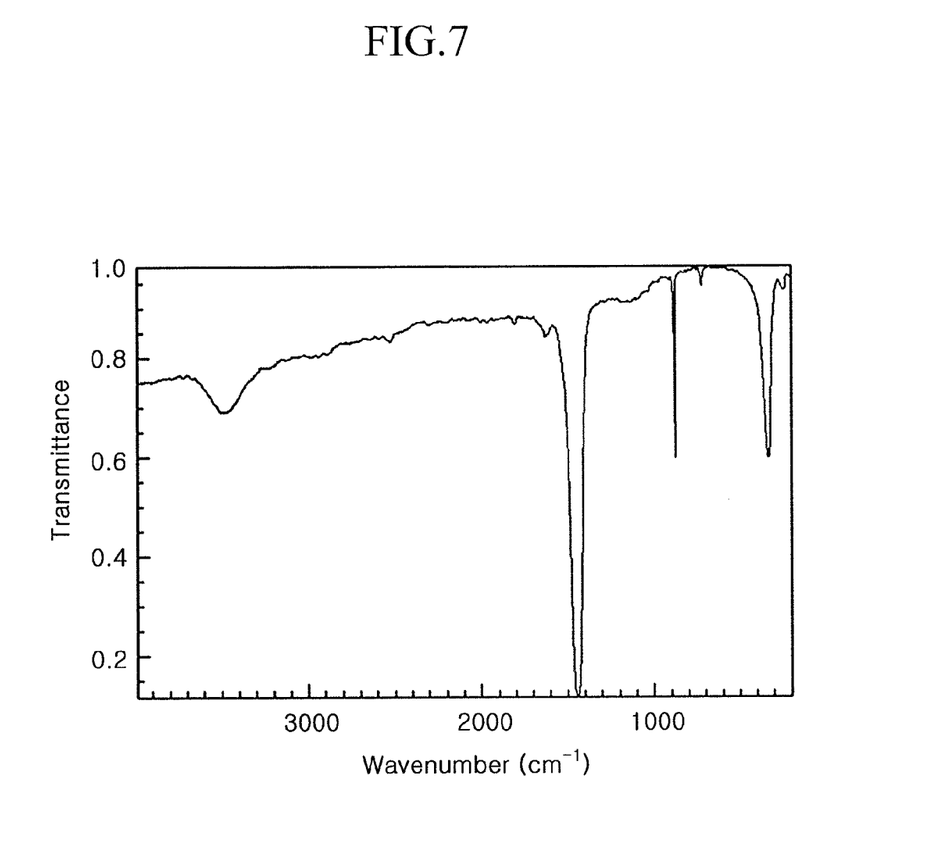
FIG. 7 illustrates a graph of an infrared absorption characteristic of calcium carbonate.

FIG. 6 illustrates a graph of an infrared absorption characteristic of moisture, e.g., water, and FIG. 7 illustrates a graph of an infrared absorption characteristic of calcium carbonate.

Referring to FIG. 6, in the case of moisture or water, the maximum infrared absorbance is represented in a region of approximately 1,400 $cm^{-1}$ to 1,600 $cm^{-1}$ and a region of approximately 3,400 $cm^{-1}$ to 3,600 $cm^{-1}$. Referring to FIG. 7, in the case of calcium carbonate, the maximum infrared absorbance is represented in a region of approximately 1,400 $cm^{-1}$ to 1,500 $cm^{-1}$ and the high transmittance of about 0.8 for the infrared absorption region (approximately 2,800 $cm^{-1}$ to 3,000 $cm^{-1}$) of the alcohol-based organic compound is represented.

Referring back to FIGS. 1 to 3, as the infrared absorption region of the filter 222 belongs or corresponds to the infrared absorption region of moisture, a part of the infrared absorption region of moisture is intercepted by the filter 222. Therefore, the filter 222 may intercept a part of the infrared absorption region of moisture, while transmitting most of the infrared absorption region of the alcohol-based organic compounds, to thereby increase the sensitivity of the infrared detection unit 30.

The filter 222 may replace a monochromator that may be included in an infrared spectrometer. Such a monochromator may be configured of a diffraction optical device having a large volume, and therefore when the monochromator is applied to the apparatus for detecting an organic compound, the configuration of the apparatus may be complicated and the volume thereof may be expanded. On the other hand, the filter 222 may be a very simple configuration and may be easily installed, such that the configuration of the apparatus 100 for detecting an organic compound may be simplified.

Figure 8:
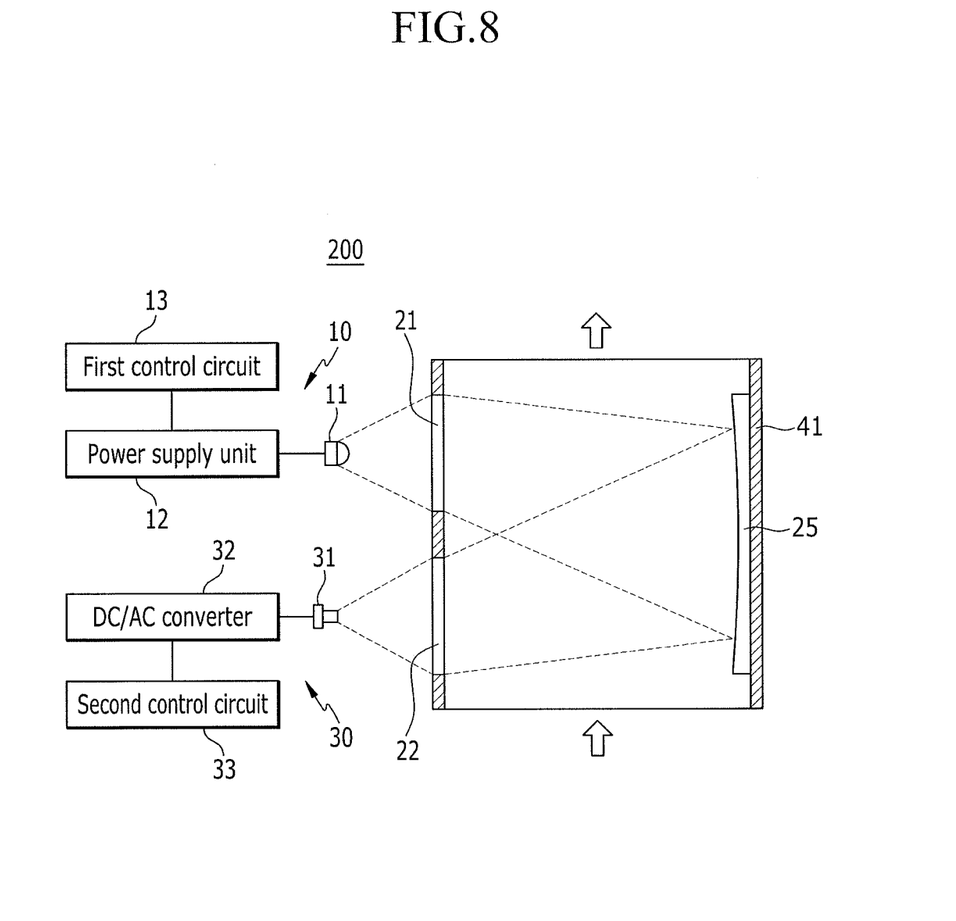
FIG. 8 illustrates a schematic diagram of an apparatus for detecting an organic compound according to a second exemplary embodiment.

FIG. 8 illustrates a schematic diagram of an apparatus for detecting an organic compound according to a second exemplary embodiment.

Referring to FIG. 8, the apparatus 200 for detecting an organic compound according to the second exemplary embodiment may be configured similarly to the first exemplary embodiment as described above, except that the infrared light emitting unit 10 and the infrared detection unit 30 may be disposed in parallel at the outside of one side of the exhaust pipe 41, and a reflector 25 may be disposed at another side of the exhaust pipe 41. The same members as the first exemplary embodiment are denoted by the same reference numerals.

The first window 21, the second window 22, and the reflector 25 may be directly disposed in the exhaust pipe 41. For example, two openings may be disposed at one side of the exhaust pipe 41, and the first window 21 and the second window 22 may be disposed in each opening via the close and seal member (see reference numeral 42 in FIGS. 2 and 3). Further, the reflector 25 may be fixed to an inner wall of the exhaust pipe 41.

The first window 21 and the second window 22 may be disposed in parallel with a flow direction of the organic compound. A direction in which the first and second windows 21 and 22 and the reflector 25 face each other may be orthogonal to a flow direction of the organic compound.

The infrared light emitting unit 10 may irradiate infrared rays to the organic compound in the exhaust pipe 41 through the first window 21, in which the infrared rays irradiated to the organic compound are reflected by the reflector 25. Then, the infrared detection unit 30 may measure the infrared absorption wavelength of the organic compound through the second window 22 to detect the concentration of the organic compound in real time.

An inner surface of the reflector 25 (facing the first and second windows 21 and 22) may be concavely formed. In this case, the infrared rays may be condensed to the second window 22 by the concave inner surface of the reflector 25, such that the performance of the infrared detection unit 30 may increase.

In an implementation, the exhaust pipe 41 illustrated in FIGS. 1 and 8 may be replaced with a wall or a door of the process chamber, such as an oven or a furnace.

Figure 9:
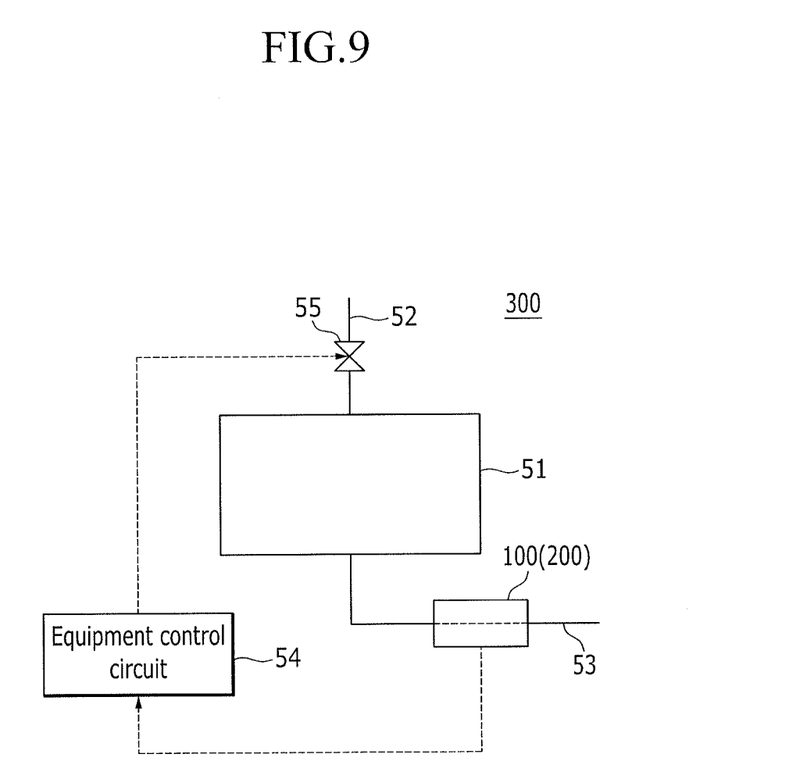
FIG. 9 illustrates a schematic diagram of an apparatus for manufacturing a display device according to a third exemplary embodiment.

FIG. 9 illustrates a schematic diagram of an apparatus for manufacturing a display device according to a third exemplary embodiment.

Referring to FIG. 9, an apparatus 300 for manufacturing a display device according to a third exemplary embodiment may include a main device 51 for cleaning or drying a substrate, a supply pipe 52 and a discharge pipe 53, the apparatuses 100 and 200 for detecting an organic compound, and an equipment control circuit 54.

The main device 51 may be configured of a cleaner or a drier, and the supply pipe 52 and the discharge pipe 53 may be connected to the main device 51. The process gas configured of the gas-phase alcohol-based organic compound may be supplied to the main device 51 through the supply pipe 52, and the process gas used for cleaning may be discharged through the discharge pipe 53. The apparatuses 100 and 200 for detecting an organic compound according to the first or second exemplary embodiment as described above may be disposed in the discharge pipe 53 to measure the concentration of the organic compound flowing in the discharge pipe 53 in real time.

The equipment control circuit 54 may be electrically connected to a flow control valve 55 that is disposed in the apparatuses 100 and 200 for detecting an organic compound and the supply pipe 52. The apparatuses 100 and 200 for detecting an organic compound may deliver the information of the concentration of the organic compound measured in real time to the equipment control circuit 54, and the equipment control circuit 54 may control the flow control valve 55 based on the provided concentration to precisely control the supply amount of the process gas.

A wet etching process for patterning a specific layer may be applied during the formation of the pixel circuit configured of the thin film transistor and the capacitor on the substrate. The substrate suffering from the wet etching may be introduced into the main device 51 to be cleaned and/or dried.

Figure 10:
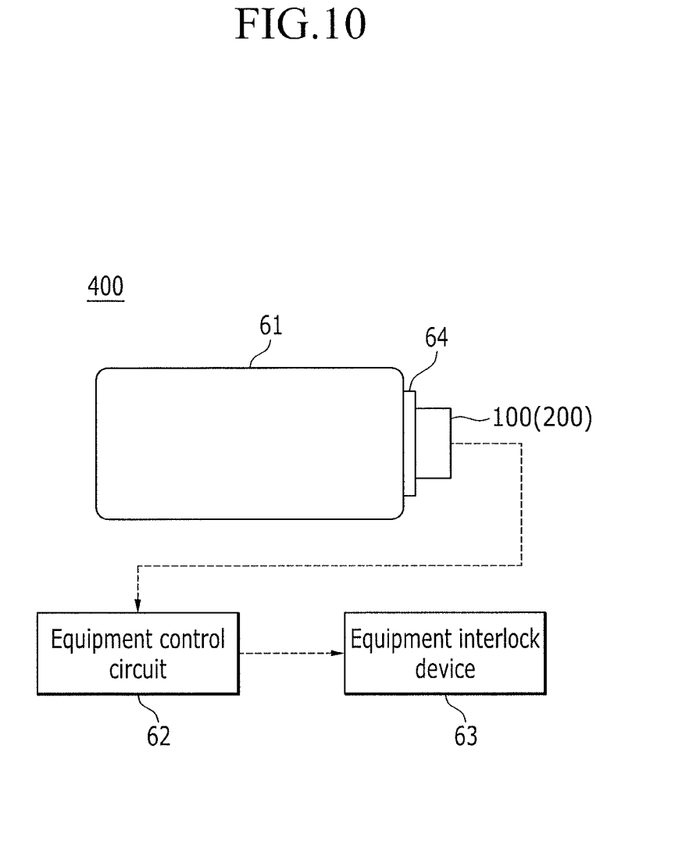
FIG. 10 illustrates a schematic diagram of an apparatus for manufacturing a display device according to a fourth exemplary embodiment.

FIG. 10 illustrates a schematic diagram of an apparatus for manufacturing a display device according to a fourth exemplary embodiment.

Referring to FIG. 10, an apparatus 400 for manufacturing a display device according to a fourth exemplary embodiment may include a process chamber 61, the apparatuses 100 and 200 for detecting an organic compound, an equipment control circuit 62, and an equipment interlock device 63.

The process chamber 61 may be an oven or a furnace that spin-coats polymer materials, e.g., polyimide, on a carrier substrate and then cures the polymer materials. A polymer layer cured in the process chamber 61 may be used as the flexible substrate of the display device.

The apparatuses 100 and 200 for detecting an organic compound according to the first or second exemplary embodiment as described above may be disposed on the wall or the door of the process chamber 61. FIG. 10 illustrates a case in which the apparatuses 100 and 200 for detecting an organic compound are disposed on the door 64 of the process chamber 61.

In the case of the apparatus 100 for detecting an organic compound according to the first exemplary embodiment, the infrared light emitting unit 10 and the infrared detection unit 30 may be disposed to face each other, having the process chamber 61 therebetween. In the case of the apparatus 200 for detecting an organic compound according to the second exemplary embodiment, the infrared light emitting unit 10 and the infrared detection unit 30 may be disposed in parallel at one side of the process chamber 61 and the reflector 25 may be disposed on the inner wall of the process chamber 61.

The apparatuses 100 and 200 for detecting an organic compound may measure the concentration of the organic compound disposed in the process chamber 61 in real time and may be electrically connected to the equipment control circuit 62 to transmit the information on the concentration of the organic compound to the equipment control circuit 62.

The equipment control circuit 62 may be electrically connected to the equipment interlock device 63. When the concentration value of the organic compound is lower than a previously input reference value, the equipment control circuit 62 may transmit the control signal to the equipment interlock device 63. The equipment interlock device 63 may include alarm devices, e.g., a display unit or a flashing light, and a power interceptor that intercepts a power supply of the process chamber 61, or the like.

The change in concentration for the gas-phase organic compound used in the atmospheric pressure process equipment may be detected in real time by using the apparatus for detecting an organic compound. Therefore, a process defect due to an interruption in the supply of or a concentration reduction of the process gas may be reduced and/or prevented. The first window and the second window included in the apparatus for detecting an organic compound may have the high chemical resistance against the organic compound and may exhibit high infrared transmittance for the infrared absorption region of the organic compound.

By way of summation and review, some atmospheric pressure equipment may not perform a concentration measurement of an organic compound in real time. Some equipment may include an ultraviolet (UV) sensor, or the like, for detecting an organic compound leaked from the equipment so as to ensure against fire occurrence. Therefore, even when a phenomenon that the process gas is not supplied, or the concentration of the process gas is reduced, may occur during the operation of the atmospheric pressure equipment, the phenomenon may not be confirmed and therefore the process defect may occur.

The embodiments provide an apparatus for detecting an organic compound that is capable of detecting a gas-phase organic compound used in atmospheric pressure process equipment in real time.

The embodiments provide an apparatus for detecting an organic compound that is capable of preventing a process defect due to a disruption in a supply of or a concentration reduction of a process gas. The apparatus may measure a concentration of a gas-phase organic compound used in an atmospheric pressure process equipment in real time.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of symbols>

100, 200: Apparatus for detecting organic compound
300, 400: Equipment for manufacturing display device
10: Infrared light emitting unit  11: Infrared light emitting element
21: First window  22: Second window
30: Infrared detection unit  31: Infrared detector
51: Main device  61: Process chamber

What is claimed is:

1. An apparatus for detecting an organic compound, the apparatus comprising:
   an infrared light emitting unit that irradiates infrared rays toward a gas-phase organic compound used as a process gas in an atmospheric pressure equipment;
   a first window that separates the organic compound from the infrared light emitting unit;
   an infrared detection unit that measures an infrared absorbance of the organic compound; and
   a second window that separates the organic compound from the infrared detection unit,
   wherein infrared absorption regions of the first window and the second window are different from an infrared absorption region of the organic compound.

2. The apparatus for detecting an organic compound of claim 1, wherein:
   the organic compound includes an alcohol-based material, and
   the first window and the second window include a silica-based material.

3. The apparatus for detecting an organic compound of claim 2, wherein the first window and the second window include any one of glass and quartz.

4. The apparatus for detecting an organic compound of claim 3, wherein the first window and the second window have an infrared transmittance of 0.7 or more in a wavenumber range of 2,800 $cm^{-1}$ to 3,000 $cm^{-1}$.

5. The apparatus for detecting an organic compound of claim 3, wherein the second window includes:
   a pair of support plates including any one of glass and quartz; and
   a filter disposed between the pair of support plates.

6. The apparatus for detecting an organic compound of claim 5, wherein the filter is made of glass that includes calcium carbonate.

7. The apparatus for detecting an organic compound of claim 6, wherein an infrared absorption region of the filter corresponds to an infrared absorption region of water.

8. The apparatus for detecting an organic compound of claim 1, wherein the infrared light emitting unit and the infrared detection unit are disposed to face each other, having one part of the atmospheric pressure equipment therebetween.

9. The apparatus for detecting an organic compound of claim 8, wherein the first window and the second window are disposed at sides of the one part via a close and seal member.

10. The apparatus for detecting an organic compound of claim 1, wherein:
    the infrared light emitting unit and the infrared detection unit are disposed in parallel at one side of one part of the atmospheric pressure equipment, and
    a reflector is disposed at another side of the one part.

11. The apparatus for detecting an organic compound of claim 10, wherein:
    the first window and the second window are disposed in parallel at the one side of the one part via the close and seal member, and
    an inner surface of the reflector facing the first window and the second window is concavely formed.

12. An apparatus for manufacturing a display device, the apparatus comprising:
    a main device that cleans or dries a substrate;
    a supply pipe that supplies a gas-phase alcohol-based organic compound to the main device;
    a discharge pipe that discharges an organic compound used for cleaning;
    an apparatus for detecting an organic compound that is disposed in the discharge pipe, the apparatus including:
      a first window and a second window including any one of quartz and glass,
      an infrared light emitting unit that irradiates infrared rays to the organic compound in the discharge pipe through the first window, and
      an infrared detection unit that measures an infrared absorbance of the organic compound through the second window; and
    an equipment control circuit that is electrically connected to the apparatus for detecting an organic compound.

13. The apparatus for manufacturing a display device of claim 12, wherein the second window further includes a filter made of glass that includes calcium carbonate.

14. The apparatus for manufacturing a display device of claim 12, wherein:
    the supply pipe is provided with a flow control valve, and
    the equipment control circuit is electrically connected to the flow control valve and controls an operation of the flow control valve depending on a concentration of the organic compound, the concentration being provided from the apparatus for detecting an organic compound.

15. An apparatus for manufacturing a display device, the apparatus comprising:
    a process chamber that has a gas-phase alcohol-based organic compound included in an inner space thereof and that cures a polymer material;
    an apparatus for detecting an organic compound that is disposed in the process chamber, the apparatus including:
      a first window and a second window including any one of quartz and glass,
      an infrared light emitting unit that irradiates infrared rays to the organic compound in the process chamber through the first window, and
      an infrared detection unit that measures an infrared absorbance of the organic compound through the second window; and
    an equipment control circuit that is electrically connected to the apparatus for detecting an organic compound.

16. The apparatus for manufacturing a display device of claim 15, wherein the second window further includes a filter made of glass including calcium carbonate.

17. The apparatus for manufacturing a display device of claim 15, wherein the equipment control circuit is electrically connected to an equipment interlock device and controls an operation of the equipment interlock device depending on a concentration of the organic compound, the concentration being provided from the apparatus for detecting an organic compound.

* * * * *